United States Patent [19]

Cohen et al.

[11] Patent Number: 5,420,265
[45] Date of Patent: May 30, 1995

[54] SEPARATION OF PHOSPHOROTHIOATE OLIGONUCLEOTIDES BY CAPILLARY GEL ELECTROPHORESIS

[75] Inventors: Aharon S. Cohen, Brookline; Maria Vilenchik, Natick, both of Mass.

[73] Assignee: Hybridon, Inc., Worcester, Mass.

[21] Appl. No.: 991,466

[22] Filed: Dec. 16, 1992

[51] Int. Cl.$^6$ .................. C07H 1/06; C07H 21/04; C07H 19/10; C07H 19/20
[52] U.S. Cl. .................. 536/25.4; 536/26.1; 536/26.72
[58] Field of Search ........................ 536/25.4

[56] References Cited

U.S. PATENT DOCUMENTS

| | | | |
|---|---|---|---|
| 2,713,041 | 7/1955 | Friedlander et al. | 260/32.6 |
| 4,865,706 | 9/1989 | Karger et al. | 204/182.8 |
| 4,865,707 | 9/1989 | Karger et al. | 204/182.8 |
| 5,003,059 | 3/1991 | Brennan | 435/6 |
| 5,098,539 | 3/1992 | Shieh | 204/182.8 |
| 5,112,460 | 5/1992 | Karger et al. | 204/182.8 |
| 5,183,885 | 2/1993 | Bergot | 536/25.41 |

FOREIGN PATENT DOCUMENTS

| | | |
|---|---|---|
| 0137753 | 4/1985 | European Pat. Off. |
| 0339780 | 11/1989 | European Pat. Off. |
| 0497448 | 8/1992 | European Pat. Off. |
| 0497480 | 8/1992 | European Pat. Off. |

OTHER PUBLICATIONS

Widhalm et al. (1991) *J. Chromatog.* 549:446–451.
Hjerten (1967) *Chromatog. Rev.* 9:122–219.
Burgers et al. (1979) *Biochem.* 18:592–596.
Edge et al. (1981) *Nature* 292:756–762.
Stec et al. (1985) *J. Chromatog.* 326:263–280.
Murakami et al. (1985) *Biochem* 24:4041–4046.
Agrawal et al. (1987) *Tetrahedron Lett.* 28:3539–3542.
Agrawal et al. (188) *Proc. Natl. Acad. Sci.* (USA) 85:7079–7083.
Sarin et al. (1988) *Proc. Natl. Acad. Sci.* (USA) 85:7448–7451.
Cohen et al. (1988) *Proc. Natl. Acad. Sci.* (USA) 85:9660–9663.
Agrawal et al. (1989) *Nucleosides and Nucleotides* 8:819–823.
Agrawal et al. (1988) *Proc. Natl. Acad. Sci.* (USA) 86:7790–7794.
Wu et al. (1989) *J. Chromatog.* 480:141–155.
Agrawal et al. (1990) *J. Chromatog.* 509:396–399.
Agrawal et al. (1990) *Nucleic Acids. Res.* 18:5419–5423.
Ansorge et al. (1990) *Nucleic Acids. Res.* 18:3419–3420.
Bigelow et al. (1990) *J. Chromatog.* 553:131–140.
Swerdlow et al. (1990) *J. Chromatog.* 516:61–67.
Cohen et al. (1990) *J. Chromatog.* 516:49–60.
Brumley et al. (1991) *Nucleic Acids. Res.* 19:4121–4126.
Chen et al. (1991) *J. Chromatog.* 559:237–246.
Swerdlow et al. (1991) *Anal. Chem.* 63:2835–2841.
Zhang et al. (1991) *Clin. Chem.* 39:1492–1496.
Bergot (1992) *J. Chromatog.* 599:35–42.
Meletev et al. (1992) *Analyt. Biochem.* 200:342–346.
Rocheleau et al. (1992) *Electrophoresis* 13:484–486.
Efcavitch in *Gel Electrophoresis of Nucleic Acids, A Practical Approach* (2d. Ed.) (Rickwood and Hames, eds.) IRL Press at Oxford University Press, New York, pp. 125–126.
Froehler (1986) *Tetrahedron Lett.* 27:5575–5578.
Garegg et al. (1986) *Tetrahedron Lett.* 27:4051–4054.
Heiger et al. (1990) *J. Chromatogr.* 516:33–48.
Guttman et al. (1991) *Anal. Chem.* 63:2038–2042.
Agrawal et al. (1992) *TIBTECH* 10:152–158.

Primary Examiner—John W. Rollins
Assistant Examiner—Gary L. Kunz
Attorney, Agent, or Firm—Lappin & Kusmer

[57] ABSTRACT

A method for separating a mixture of 5'-phosphorothioate mononucleotides, a mixture of 5'-phosphorothioate oligonucleotides, or a mixture of both 5'-phosphorothioate mononucleotides and 5'-phosphorothioate oligonucleotides comprising electro- phoresis through a gel of at least 12% polymerized linear acrylamide containing at least 50% formamide or other denaturing organic solvent. This method can resolve phosphorothioate oligonucleotides differing by only a single base. Samples of less than 1 nanogram in microliter volumes can be conveniently handled.

12 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

CGTATAGCCT GATGTCATAG CCGAT        25

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:2:

GACTCGAGGT CTGCTAACCT AGAT        24

SEPARATION OF PHOSPHOROTHIOATE OLIGONUCLEOTIDES BY CAPILLARY GEL ELECTROPHORESIS

FIELD OF THE INVENTION

This invention relates to the separation of synthetic oligonucleotides. More particularly, this invention relates to the separation, purification, and characterization of 5'-substituted mononucleotides and phosphate backbone-modified analogs of oligonucleotides by high performance capillary gel electrophoresis.

BACKGROUND OF THE INVENTION

Oligonucleotides that are complementary or "antisense" to specific genes or RNA sequences are relatively small, synthetic molecules having an average molecular weight of about 10 kilodaltons (kD). These antisense molecules have had widespread use in the field of selective gene regulation with consequent therapeutic implications. Phosphate backbone modification of such oligonucleotides provides nuclease resistance and greatly enhances the usefulness of these analogs. Such modifications include the substitution of phosphodiester internucleotide linkages with linkages such as methylphosphonates (Murakami et al. (1986) Biochem. 24:4041-4046; Agrawal et al. (1987) Tetrahedron Lett. 28:3539-3542; Sarin et al. (1988) Proc. Nat. Acad. Sci. (U.S.A.) 85:7448-7451), phosphorothioates (Burgers et al. 1979 Biochemistry 18:592-596; Agrawal et al. (1988) Proc. Natl. Acad. Sci. (U.S.A.) 85:7079-7083; Agrawal et al. (1989) Nucleosides and Nucleotides 8:819-823; Agrawal et al. (1989) Proc. Natl. Acad. Sci. (U.S.A.) 86:7790-7794), and phosphoramidates (Agrawal et al. (1988) Proc. Natl. Acad. Sci. U.S.A. 85:7079-7083; Agrawal et al. (1989) Nucleosides and Nucleotides 8:819-823).

Of special interest are phosphorothioate analogs in which one non-bridging oxygen atom has been substituted for a sulfur atom on the phosphate group in each internucleotide phosphate linkage. This modification is a conservative substitution which increases nuclease resistance without significantly impairing the hybridization of the antisense molecule with target mRNA. As synthesized, these analogs are usually found as diastereomeric mixtures due to chirality at their phosphorous group. In a context of new drug research, development and manufacturing of such analogs requires that the issues of oligomer length, base composition, base sequence, chemical purity, and stereochemical purity be successfully addressed.

Synthetic oligonucleotides are presently a standard reagent in most laboratories using molecular biology techniques. As synthesized, these oligomers generally exist as mixtures of truncated oligomers in addition to the desired oligomer. Since the purity and chemical identity of a particular oligonucleotide is crucial to many applications, the ability to characterize synthetic oligonucleotides analogs on a routine basis is important.

The absolute length and the degree of length heterogeneity of prepared oligonucleotides have been assessed by electrophoresis in high resolution denaturing polyacrylamide slab gels (PAGE) (see, e.g., Current Protocols in Molecular Biology, Green Publishing and Wiley Interscience, N.Y., 1988) and by capillary gel electrophoresis through polyacrylamide cross-linked gels (6% T, 5% C) (Hjerten (1967) Chromatographic Rev. 9:122-213) modified with from 10% to less than 30% (volume:volume) formamide (Rocheleau et al. (1992) Electrophoresis 13:484-486). Detection of oligonucleotides separated on such gels has been accomplished by autoradiography and laser-induced fluorescence. Ultrathin slab gels (less than 100 μm in thickness) have also been used for high speed DNA sequencing (Brumley et al. (1991) Nucleic Acids Res. 19:4121-4126; Ansorge et al. (1990) Nucleic Acids Res. 18:3419-3420). Alternative separation methods include ion exchange chromatography, reversed phase high pressure liquid chromatography (HPLC), and gel high performance capillary electrophoresis (HPCE) (see, e.g., Edge et al. (1981) Nature 292:756-762; U.S. Pat. No. 4,865,707).

Oligonucleotides with phosphorothioate linkages are more difficult to resolve than phosphodiester-linked DNA due to the existence of diastereomer isomers (2n, where n = the number of chiral centers, which is equivalent to the number of phosphate groups). In addition, difficulty in resolution may be due to increased hydrophobicity of the former. These molecules, while separated, interact hydrophobically with ion exchange column supports and in many cases co-elute. Thus, they cannot be separated by the above methods in their existing formats.

The separation of phosphorothioate oligonucleotide analogs is problematic for other reasons as well. When phosphorothioate oligonucleotides are assembled using either methoxyphosphoramidite or H-phosphate chemistry, they are in the form of diastereomeric mixtures due to chirality at their phosphorous groups. As a result, although they migrate through polyacrylamide gels and HPLC columns like their corresponding phosphodiester counterparts, phosphorothioate oligonucleotides give broader peaks and run more slowly than phosphodiesters because of their increased hydrophobicity. They are also known to interact with the HPLC column support. In addition, phosphorothioates run into stereochemical problems when separated by reversed phase HPLC. General analytical methods have not been devised for establishing the ratio of the optical isomers at each unsymmetrical substitution phosphorous linkage in an analog having many such sites of local chirality.

HPLC of oligodeoxyribonucleotides containing one or two phosphorothioate internucleotide linkages using a reversed-phase column (RP-HPLC) has been reported (Stec et al. (1985) J. Chromatogr. 326:263-280; Agrawal et al. (1990) Nucleic Acids Res. 8:5419-5423). However, this method is of limited use because of the small differences in the hydrophobicity of these analogs with increasing chain length (Agrawal et al. (1990) J. Chromatogr. 509:396-399).

Oligodeoxyribonucleotide phosphorothioates containing 10 or fewer nucleotides has also been achieved by HPLC on strong anion-exchange (SAX) columns (Agrawal et al. (1990) J. Chromatogr. 509:396-399). In this method, oligonucleotide phosphorothioates were converted to their phosphodiester counterparts in one step, and then were analyzed by HPLC. Unfortunately, oligonucleotides phosphorothioates containing more than 10 nucleotides can not be analyzed by this method because of their strong interaction with the SAX medium. Thus the separation of oligonucleotide phosphorothioates by this method is limited by its oligonucleotide length dependency.

Length-dependent separation of phosphorothioate analogs by HPLC using a weak anion-exchange (WAX)

column has also been accomplished (Meletev et al. (1992) Analyt. Biochem. 200:342-346). However, the peaks obtained were broader than those obtained for their phosphodiester counterparts, possibly because of their diastereomeric backbone. Ion-pair HPLC has also been used to analyze oligonucleotide phosphorothioates (Bigelow et al. (1990) J. Chromatogr. 533:131-140), but length-dependent separation was not achieved.

Thus, what is needed are better analytical methods of separating oligonucleotide analogs cleanly, rapidly, efficiently, and which are not limited by the size range of the molecules being analyzed.

SUMMARY OF THE INVENTION

A novel gel substrate and method of its use have been developed for the separation of mixtures of 5'-substituted mononucleotide analogs and oligonucleotide analogs with artificial internucleotide linkages differing by only a single base. An advantage to this method is the relative ease by which samples of less than 1 ng and in μl or smaller volumes can be conveniently handled with on-line UV detection. Relative to slab gel and on-line UV regular gel HPCE operation, this new formulation can be very useful for in process analysis as well as for purity assessment of antisense in the pharmaceutical industry.

As used herein, a "5'-substituted mononucleotide analog" is a base, including purines and pyrimidines or analogs thereof, attached to the 1' end of a deoxyribose or ribose sugar, which is attached at its 5' position to a chemical group other than the phosphate group found in native nucleotides. Preferable chemical groups include methyl phosphonates, phosphorothioates, phosphoramidates, and phosphorodithioates.

An "oligonucleotide analog," as used herein, is a molecule of at least two ribonucleotides or deoxyribonucleotides which are covalently linked via at least one synthetic, non-phosphodiester linkage. A "synthetic internucleotide linkage" is a linkage other than a phosphodiester linkage between the 5' end of one nucleotide and the 3' end of another nucleotide in which the 5' internucleotide phosphate has been replaced with any number of chemical groups. Preferable synthetic linkages include methyl phosphonates, phosphorothioates, phosphoramidates, and phosphorodithioates.

The substrate of the invention includes at least 12% T polymerized acrylamide in at least 50% and preferably 60% (volume:volume) organic solvent, the organic solvent being a denaturing agent. The term "T" refers to the percent of monomers (mass:volume). The acrylamide may be non-cross-linked in some aspects of the invention. A preferable organic solvent is formamide present at a concentration of at least 60% (volume:volume). In some embodiments of the invention, the substrate contains about 12% to 20% T polyacrylamide, with from about 13% to 18% T being optimal. A linear gradient of about 13% to 18% T polyacrylamide is included in some aspects of the invention. In other embodiments, the invention includes a substrate containing 18% T polyacrylamide, and may further include urea.

This invention also provides a method of separating 5'-substituted mononucleotide analogs and oligonucleotide analogs with synthetic internucleotide linkages using the above-described substrate. The method includes contacting the substrate, which is in a high performance capillary, with the mononucleotide and oligonucleotide analogs to be separated. An electric field greater than 200 volts/centimeter is applied across the gel in the capillary, and the separated mononucleotide and oligonucleotide analogs detected. In preferred embodiments of the invention, an electric field of about 400 volts/cm is applied across the gel substrate.

Molecules capable of being separated by this method include mononucleotide and oligonucleotide analogs having from 1 to 50 bases. This method is also useful for separating mono- and oligonucleotide analogs having from 1 to 100, and from 1 to 300 bases.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
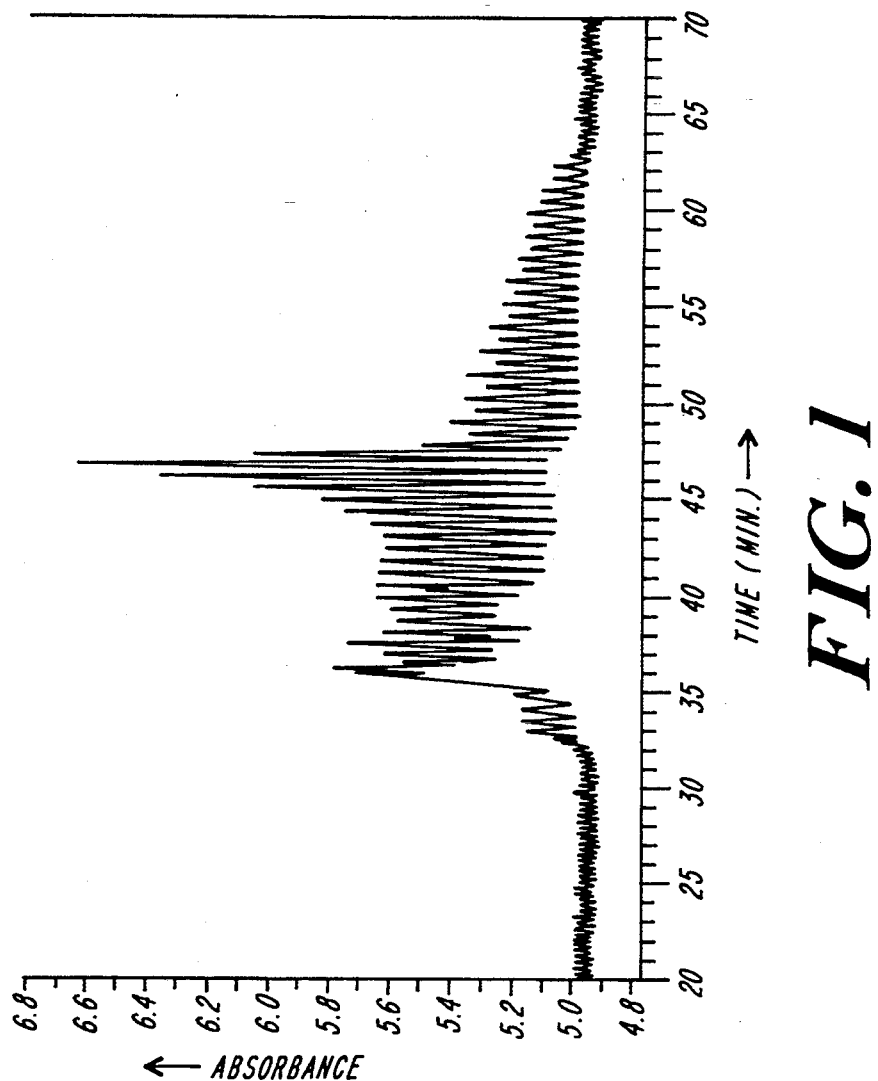
FIG. 1 is an electropherogram demonstrating the electrophoretic separation by high performance capillary electrophoresis of phosphorothioate failure sequences ranging in length from 1 to 50 bases in length.

This invention provides a novel gel substrate and methods of using that substrate to separate 5'-substituted mononucleotides and phosphorothioate oligonucleotide analogs differing by only one base.

Gel high performance capillary electrophoresis (HPCE) utilizing the novel gel substrate of the invention has a unique position in the field of oligodeoxynucleotide separation due to its resolution power, ability to determine purity, speed, and automation. Because of the low current generated ($\mu$A) from the narrow bore columns (25 to 100 $\mu$m, inner diameter), high electric fields (hundreds of volts/cm) without excess Joule heating can be employed, resulting in very rapid, high resolution separations. As an instrument technique, gel HPCE is highly reproducible, is amenable to automation, and is thus a powerful alternative tool for antisense analysis.

Traditional capillary electrophoresis suggests the application of electric fields lower than 300 V/cm with low ionic strength buffer (not higher than 0.1 M Tris-borate-EDTA (TBE) and low gel concentration in aqueous media for the separation of oligonucleotides. However, it has been discovered that the use of 0.2 M TBE buffer and an electric field of at least 300 V/cm gives very high resolution in certain gel substrates for the separation of oligonucleotide analogs.

The substrate which is used to fill the capillary is a polymer gel such as polyacrylamide. The gel need not be crosslinked. It is important that the concentration of acrylamide in the capillary be 12% T or higher to achieve this kind of resolution and efficiency. No gradient of acrylamide is required, but linear gradients of from about 12% to 20% T, or more preferably, from about 13% to 18% T may be used. The acrylamide must be suspended in at least 50% (volume:volume) organic solvent. Useful organic solvents are also denaturing agents which keep the oligonucleotides from assuming secondary structure, an obstacle to clean separation. One particularly useful organic solvent is formamide. To improve denaturation even more, a high concentration of urea (7 to 8.3 M) may also be added. Polymerization may be achieved by adding ammonium persulfate and N,N,N', N'-tetramethylenediamine (TEMED) to the acrylamide solution. The polymerizing gel solution is then placed into the capillary where it polymerizes. A useful capillary is a microcapillary column made of fused silicon, as described in U.S. Pat. Nos. 4,865,706 and 5,112,460.

The molecules which can be successfully separated on this gel substrate include 5'-substituted mononucleotides and ol igonucleotide analogs having other than phosphodiester internucleotide linkages. Such 5' substitutions and linkages include, but are not limited to, phosphorothioates, phosphorodithioates, methylphosphonates, and phophoramidates. The preparation of these molecules is well known in the art (reviewed in Agrawal et al. (TIBTECH (1992) 10:152-158). For example, monomeric and oligomeric phosphorothioate analogs can be prepared using methods well known in the field such as methoxyphosphoramidite (see, e.g., Agrawal et ai. (1988) Proc. Natl. Acad. Sci. (U.S.A.) 85:7079-7083) or H-phosphoriate (see, e.g., Froehler (1986) Tetrahedron Lett. 27:5575-5578) chemistry. The synthetic methods described in Bergot et al. (J. Chromatog. (1992) 559:35-47) can also be used. The products of these syntheses may include failure sequences as well as the desired oligonucleotide sequence. The failure sequences have at least one less base than the desired oligonucleotide, but the position of the missing base is unknown without subsequent sequencing analysis.

In order to separate the failure sequences from the desired oligonucleotides so produced, or in order to distinguish, characterize, and isolate different desired monomeric and/or oligomeric analogs from each other, the molecules to be examined are analyzed by HPCE using a capillary electrophoresis apparatus. Such as instrument is well known in the field (see, e.g., Cohen et al. (1988) Proc. Natl. Acad. Sci. (USA) 85:9660-9663). The molecules to be separated are injected into the capillary by siphoning (in the case of open tube applications). Alternatively, the sample may be electrophoretically injected into the column by dipping the cathodic end of the capillary into the sample solution and applying a field of 400 v/cm for 1 to 3 sec. The sample is then run through the gel, and the separated analogs detected by UV, infrared, fluorescence, laser-induced fluorescence or other external monitoring methods.

Figure 3:
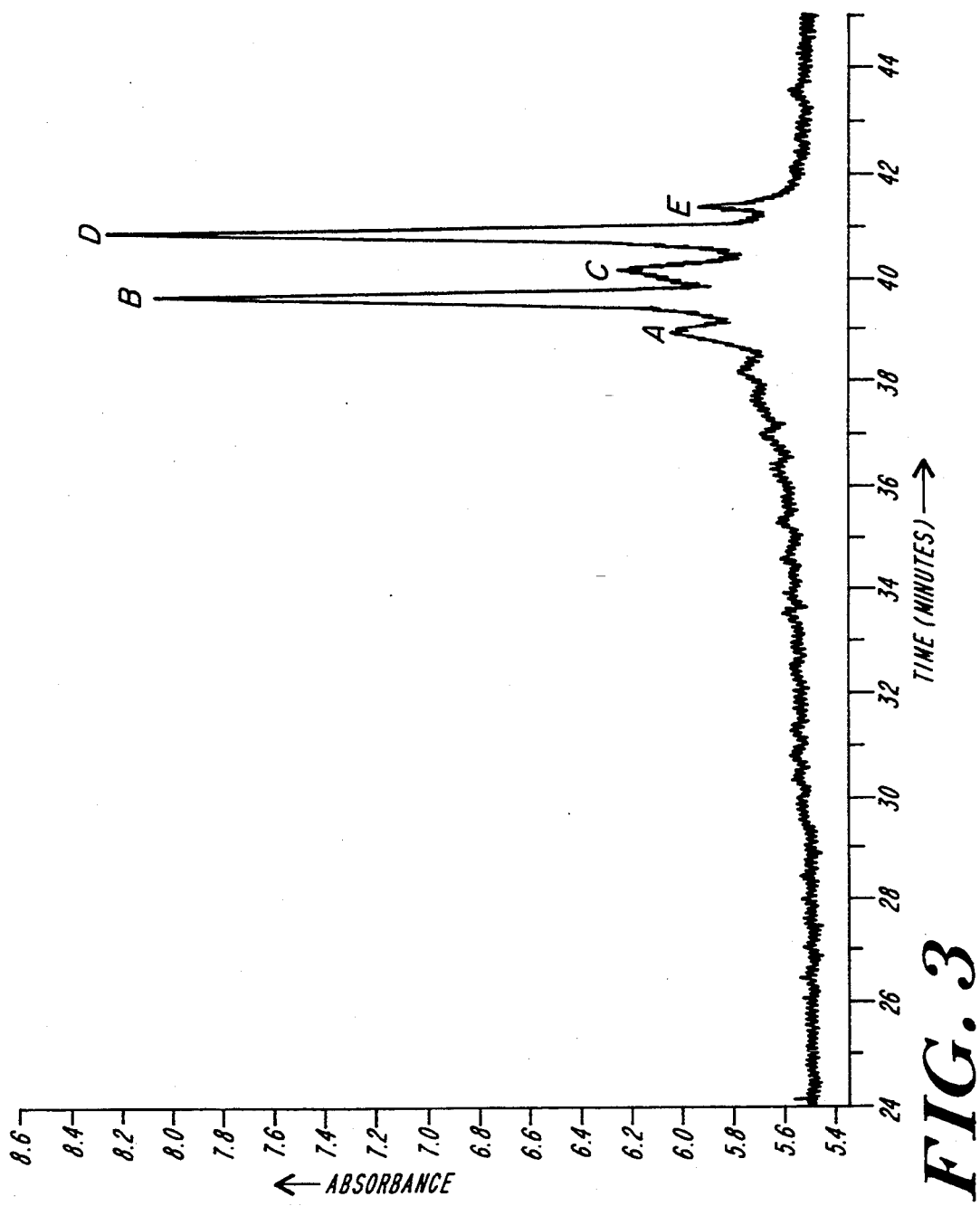
FIG. 3 is an electropherogram demonstrating the electrophoretic separation of a mixture of the 25mer (SEQ ID NO:1), the 24mer (SEQ ID NO:2), and failure sequences resulting from the syntheses of these phosphorothioate oligonucleotide analogs. Peak A represents the putative 23mer failure sequence from 24mer (SEQ ID NO:2) synthesis; peak B represents the 24mer (SEQ ID NO:2); peak C represents the putative 24mer failure sequence from 25mer (SEQ ID NO:1) synthesis; peak D represents the 25mer (SEQ ID NO:1); and peak E is unknown.

As demonstrated by the electropherogram in FIG. 1, this method enables the separation of oligonucleotide analogs differing in length by only one base in length. Furthermore, this method separates oligonucleotide analogs having the same length but differing in base sequence, as shown in FIG. 3.

The following examples illustrate the preferred mode of making and practicing the present invention, but are not meant to limit the scope of the invention since alternative methods may be utilized to obtain similar results.

EXAMPLES

1. HPCE Apparatus

The capillary electrophoresis apparatus with UV detection and the preparation of gel-filled capillary for the separation of DNA molecules are essentially the same as described in Cohen et al. (Proc. Natl. Acad. Sci. (U.S.A.) (1988) 85:9660-9663) and Heiger et al. (J. Chromatogr. (1990) 516:33-48). A 30 kV, 500 μA direct current high voltage power supply (Model ER/DM; Glassman, Whitehouse Station, N.J.) was used to generate the potential across the capillary.

2. Preparation of Gel-Filled Capillaries

Fused-silica capillary tubing (Polymicro Technologies, Phoenix, Ariz.) with inner diameter of 75 μm, outer diameter of 375 μm, effective length of 20 cm, and total length of 30 cm, was treated with (methylacryloxypropyl)trimethoxysilane (Petrarch Systems, Bristol, Pa.) and then filled with a carefully degassed 13 to 18% T polymerizing linear polyacrylamide in aqueous or formamide solution in 0.2 M TBE buffer (0.2 M Tris borate, 4 mM EDTA), pH 8.3, with 7 to 8.3 M urea. Alternatively, capillaries were filled with a degassed solution of 13% or 18% T linear polyacrylamide. Polymerization was achieved by adding ammonium persulfate solution and TEMED. To remove impurities from the polyacrylamide gel, the capillary gel column was preelectrolyzed at 6 kV for 30 to 60 minutes. During electrophoresis, the capillary was maintained at room temperature. Ultra-pure Trizma base, urea, acrylamide, and EDTA were purchased from Schwartz/Mann Biotech (Cleveland, Ohio). TEMED and ammonium persulfate were purchased from Bio-Rad (Richmond, Calif.).

3. Preparation of Oligonucleotides

The oligonucleotide phosphorothioate 25mer 5'-CGTATAGCCTGATGTCATAGCCGAT-3' (SEQ ID NO:1), 24-mer 5'-GACTCGAGGTCTG-CTAACCTAGAT-3'(SEQ ID NO:2), and the failure sequences from the syntheses of various oligomers having a length of up to 50 bases (base sequences unknown) were synthesized in house using the procedure of Beaucage et al. (U.S. Pat. No. 5,003,097), herein incorporated by reference. Briefly, oligodeoxyribonucleotides were synthesized on an automated synthesizer (Model 8700, Milligen/Biosearch, Bedford, Mass.). Both normal phosphodiester oligodeoxyribonucleotides and their phosphorothioate analogues were assembled using H-phosphonate chemistry (Andrus et al. (1988) Tetrahedron Lett. 29:61; Gregg et al. (1987) Tetrahedron Lett. 27:4051). Synthesis was carried out on a 10-μmol scale, and after the chain elongation cycles the controlled pore glass support-bound oligonucleoside. H-phosphonate was treated either with 0.2 M sulfur in carbon disulfide:pyridine: triethylamine (12:12:1, volume:volume) to generate phosphorothioate internucleotide linkages. Deprotection of oligodeoxyribonucleotide was carried out with concentrated ammonia at 55° C. for 8 h. Deprotected oligodeoxyribonucleotides were then resuspended in distilled water.

4. Separation of Oligonucleotides

Samples were electrophoretically injected into the column by dipping the cathodic end of the capillary into the sample solution and applying a voltage of 400 V/cm for 2 seconds. Separation was achieved at a typical applied field of 400 V/cm. Each column was used for multiple injections. Periodically, a short section of the capillary at the injection end was trimmed.

Figure 2:
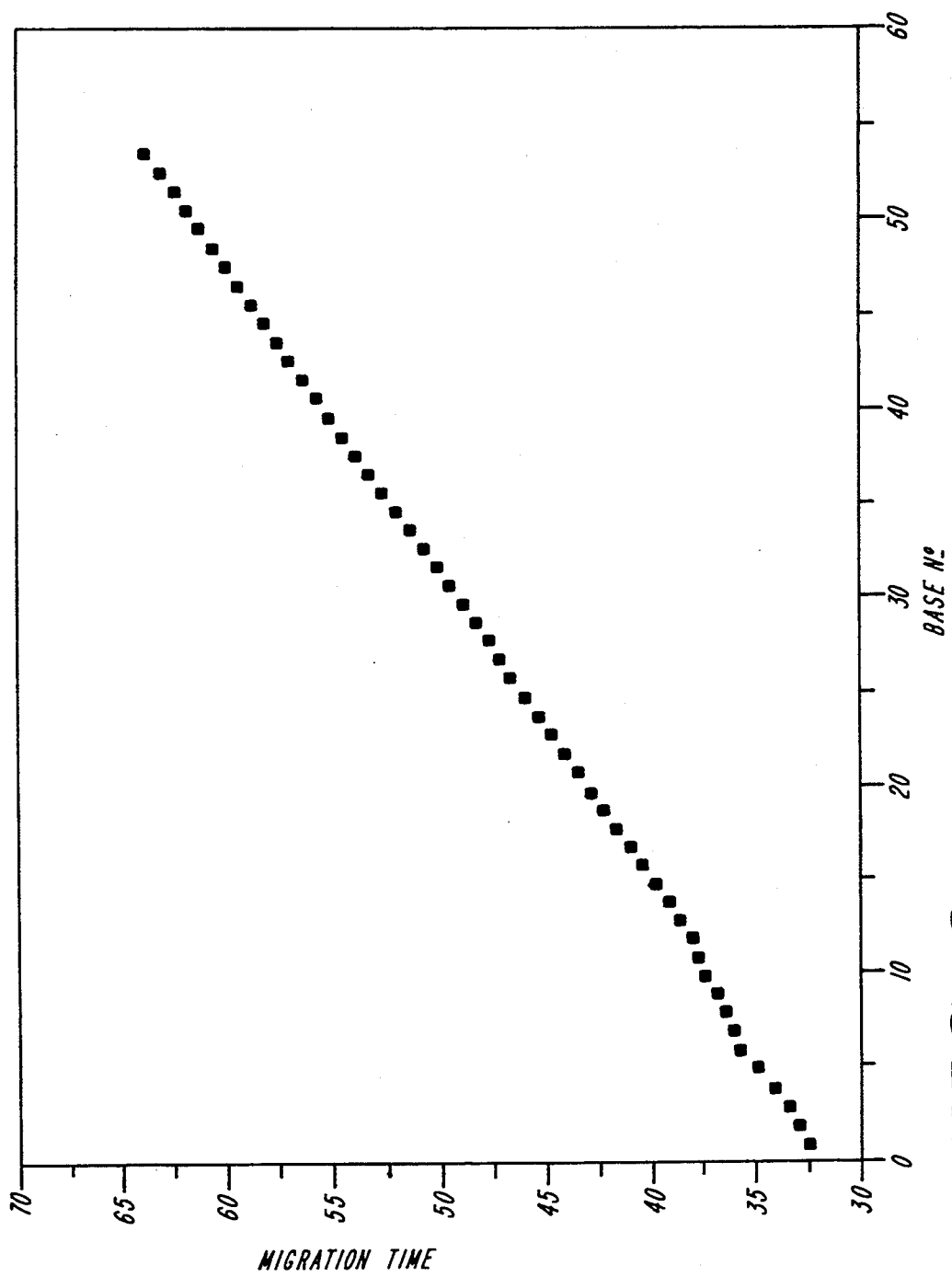
FIG. 2 is a calibration plot of migration time of the analogs separated in FIG. 1 versus base length in the analog.

The failure sequence sample (containing oligonucleotides varying in length from 1 to 50 bases) was suspended in water with final concentration 500 ng/ml. This sample was separated on a capillary containing 15% T linear polyacrylamide. The column was developed with 60% formamide, 0.2 M TBE buffer, 8.3 M urea, pH 8.3. Electrophoresis was conducted under an applied electric field of 400 volts/cm and a current of 12 $\mu A$ over a 20 cm migration distance. The results are shown in FIG. 1. When migration time was examined with respect to fragment length, a linear relationship ($r^2 = 0.9999$) was observed (FIG. 2). This linear behavior of the phosphorothioate analogs is indicative of the lack of peak compression, and of migration according to molecular weight or size, each being important elements of successful oligonucleotide separation.

A sample containing a mixture of the 24mer (SEQ ID NO:2) and the 25mer (SEQ ID NO:1) phosphorothioate analogs (having different sequences but the same length) was suspended in water to final concentration 400 ng/ml. The sample was run on a capillary containing 13% T, 0% C, 7 M urea, 0.2 M TBE, pH 8.3. (The term "c" refers to a fraction: the amount of crosslinked polymer over the total monomer and crosslinked monomer). Electrophoresis was conducted under an electric field of 400 volts/cm and a current of 12 $\mu A$ over a 20 cm migration distance. The results are shown in FIG. 3. The time window between elution of the 24mer and elution of the 25mer is large enough to accommodate an additional peak. This peak is presumed to be a failure sequence of the synthesized 25mer and is therefore a 24mer since this peak is migrating directly after the 25mer under denaturing conditions. The two 24mers are separated due to the difference in their base sequences.

5. Detection Method

Oligonucleotides were monitored by UV detection at wavelength 270 nm using a Spectra-100 spectrophotometer (Spectra Physics, San Jose, Calif.). The data were stored on an Ace IBM compatible PC computer via an analog to digital (A/D) converter (Model 970, Nelson Analytical, Cupertino, Calif.).

Those skilled in the art will recognize, or be able to ascertain, using no more than routine experimentation, numerous equivalents to the specific substances and procedures described herein. Such equivalents are considered to be within the scope of this invention, and are covered by the following claims.

---

---

What is claimed is:

1. A method of separating a mixture of 5'-phosphorothioate mononucleotides, a mixture of 5'-phosphorothioate oligonucleotides of up to 300 bases in length, or a mixture of both 5'-phosphorothioate mononucleotides and 5'-phosphorothioate oligonucleotides of up to 300 bases in length, the method comprising the steps of:

(a) providing a substrate in a high performance capillary, the substrate comprising at least 12% T polymerized linear (uncrosslinked) acrylamide in at least 50% (volume:volume) organic solvent, the organic solvent being a denaturing agent;

(b) contacting the substrate with the mononucleotides and/or oligonucleotides to be separated;

(c) applying an electric field greater than at least 200 volts/cm across the gel in the capillary; and (d) detecting the separated mononucleotides and/or oligonucleotides.

2. The method of claim 1 wherein the providing step (a) comprises providing a substrate containing from about 12% to 20% T polyacrylamide.

3. The method of claim 2 wherein the providing step (a) comprises providing a substrate containing from about 13% to 18% T polyacrylamide.

4. The method of claim 3 wherein the providing step (a) comprises providing a substrate containing about 18% T polyacrylamide.

5. The method of claim 3 wherein the providing step (a) comprises providing a substrate containing a linear gradient of from about 13% to 18% T polyacrylamide.

6. The method of claim 1 wherein the providing step (a) comprises providing a substrate containing the organic solvent formamide.

7. The method of claim 6 wherein the providing step (a) comprises providing a substrate containing about 60% (volume:volume) formamide.

8. The method of claim 1 wherein the providing step (a) comprises providing a substrate further containing urea.

9. The method of claim 1 wherein the contacting step (b) comprises contacting the substrate with oligonucleotides having from 1 to 100 bases.

10. The method of claim 1 wherein the contacting step (b) comprises contacting the substrate with oligonucleotides having from 1 to 50 bases.

11. The method of claim 1 wherein the applying step comprises applying an electric field of about 400 volts/cm across the gel substrate.

12. A method of separating a mixture of 5'-phosphorothioate mononucleotides, a mixture of 5'-phosphorothioate oligonucleotides, or a mixture of both 5'-phosphorothioate mononucleotides and 5'-phosphorothioate oligonucleotides, the method comprising the steps of:
  (a) providing a polymerized, gel substrate in a high performance capillary, the substrate comprising 13% to 18% T linear (uncrosslinked) polyacrylamide in 60% (volume:volume) formamide;
  (b) contacting the gel in the capillary with the mononucleotides and oligonucleotides to be separated, the mononucleotides and oliqonucleotides having from 1 to 50 bases;
  (c) applying an electric field of about 400 volts/cm across the gel in the capillary; and
  (d) detecting the separated mononucleotides and oligonucleotides.

* * * * *